United States Patent
Nakamura et al.

(10) Patent No.: US 6,749,562 B2
(45) Date of Patent: Jun. 15, 2004

(54) VIDEO ENDOSCOPE AND SYSTEM INCORPORATING THE SAME

(75) Inventors: Tetsuya Nakamura, Saitama-ken (JP); Hirohisa Ueda, Saitama-ken (JP); Rensuke Adachi, Tokyo (JP); Stephen F. Fulghum, Jr., Marblehead, MA (US)

(73) Assignees: PENTAX Corporation, Tokyo (JP); Newton Laboratories Inc., Woburn, MA (US)

( * ) Notice: Subject to any disclaimer, the term of this patent is extended or adjusted under 35 U.S.C. 154(b) by 0 days.

(21) Appl. No.: 09/988,239

(22) Filed: Nov. 19, 2001

(65) Prior Publication Data
US 2002/0062064 A1 May 23, 2002

(30) Foreign Application Priority Data
Nov. 17, 2000 (JP) ........................................ 2000-351157

(51) Int. Cl.⁷ ................................................. A61B 1/05
(52) U.S. Cl. ........................................ 600/181; 600/160
(58) Field of Search ................................ 600/160, 176, 600/181, 476; 359/350, 885

(56) References Cited

U.S. PATENT DOCUMENTS

| | | | |
|---|---|---|---|
| 4,987,884 A | * | 1/1991 | Nishioka et al. ............... 128/6 |
| 5,772,580 A | | 6/1998 | Utsui et al. |
| 5,876,327 A | * | 3/1999 | Tsuyuki et al. ............. 600/112 |
| 5,936,016 A | * | 8/1999 | Lareginie et al. ............. 524/94 |
| 5,954,633 A | * | 9/1999 | Hirata ......................... 600/108 |
| 6,099,466 A | | 8/2000 | Sano et al. |
| 6,471,636 B1 | * | 10/2002 | Sano et al. ................. 600/109 |

FOREIGN PATENT DOCUMENTS

| | | |
|---|---|---|
| JP | 9-243935 | 9/1997 |
| WO | 99/18845 | 4/1999 |

* cited by examiner

Primary Examiner—John P. Leubecker
Assistant Examiner—Aaron Roane
(74) Attorney, Agent, or Firm—Greenblum & Bernstein, P.L.C.

(57) ABSTRACT

An objective lens is substantially telecentric toward the image side, and provided with an ultraviolet cut coating on its rearmost surface. An imaging plane of a CCD is arranged near a position where an image of an object is formed through the objective lens. An ultraviolet and infrared cut filter is interposed between the objective lens and the CCD. The cut coating and the cut filter have a total transmittance of 0.1% or lower for ultraviolet light.

9 Claims, 4 Drawing Sheets

VIDEO ENDOSCOPE AND SYSTEM INCORPORATING THE SAME

BACKGROUND OF THE INVENTION

1. Field of the Invention

The present invention relates to a video endoscope system which obtains image data of a body cavity by picking up images of the inside of the body cavity formed from auto-fluorescence caused by its living tissues for a diagnosis thereof. The present disclosure relates to subject matter contained in Japanese Patent Application No. 2000-351157 (filed on Nov. 17, 2000), which is expressly incorporated herein by reference in its entirety.

2. Description of the Related Art

A video endoscope system which picks up image formed from auto-fluorescence caused by living tissue as an object of examination irradiated with excitation light such as ultraviolet light to output image data representative of the captured images has been utilized. It is known that diseased living tissue causes auto-fluorescence at a lower intensity than that of normal tissue. Therefore, by observing the images formed from the auto-fluorescence, an operator can diagnose a region where intensity of the fluorescence is low as a diseased part.

This type of a video endoscope system includes a light source unit for emitting excitation light, an illumination optical system for guiding the emitted excitation light to an object of examination, an objective lens for forming an image of the object, and a CCD for converting the image of the object into video signals. When irradiated with the excitation light guided through the illumination optical system, the object generates auto-fluorescence. Thereupon, the objective lens receives the fluorescence, as well as the excitation light reflected by the surface of the object. An optical filter to cut down the ultraviolet wavelength components is interposed between the objective lens and the CCD. The fluorescence transmitted through the objective lens passes through the filter, while the excitation light which transmitted through the objective lens is cut down by the optical filter. The fluorescence passed through the optical filter forms an image near the imaging plane of the CCD. Meanwhile, despite filtering by the optical filter, a small amount of the excitation light transmits through the optical filter to enter the CCD. By such a reason, the image data output from the video endoscope system contains not only a component of the image formed from the auto-fluorescence caused by the object but also a component of the image formed from the excitation light. Accordingly, when the video signals are transmitted to the monitor, the image formed from the excitation light are superposed on the image formed from the auto-fluorescence. In other words, the excitation light interferes with the image formed from the auto-fluorescence, so that the operator is unable to precisely understand the condition of the auto-fluorescence of the object.

In order to eliminate the adverse effects due to the excitation light from the fluorescence image, the excitation light which enters the CCD must further be reduced. For that purpose, the transmittance of the optical filter which is composed of a large number of films deposited on a substrate with respect to the excitation light could be further lowered, if the number of the deposited films is increased. However, an increase in the number of deposited films will lead to an increase in the stress resulting in the optical filter being more likely to crack. This will cause a decrease in the yields of the optical filter in its fabrication process. Thus, increasing the number of deposited films of the optical filter is not a practical idea.

SUMMARY OF THE INVENTION

An object of the present invention is to provide a video endoscope which can eliminate the influence caused by excitation light not only with an optical filter, and a video endoscope system equipped with such an endoscope.

To achieve the object, a video endoscope according to the present invention includes: an objective lens system having a lens surface provided with a coating for transmitting visible light while reducing excitation light for exciting a living tissue to cause auto-fluorescence; an image pickup device for converting an image of an object formed through the objective lens system into video signal; and an optical filter interposed between the objective lens system and the image pickup device for transmitting visible light while reducing the excitation light. Further, a video endoscope system according to the present invention includes the above described video endoscope, an excitation light irradiating unit which irradiates excitation light to the object, and a processor which generates and outputes fluorescence video data corresponding to the image of the object formed from the auto-fluorescence caused by the object, based on the video signal obtained by the image pickup device of the video endoscope.

When the object is irradiated with the excitation light, both the auto-fluorescence emitted from the living tissue of the object and the excitation light reflected by the surface of the object enter the objective lens. However, according to the present invention, the excitation light is cut down by the coating provided to the objective lens system. The cut down excitation light is further cut down by the optical filter, which allows only the auto-fluorescence to reach the image pickup device. This image pickup device converts the image formed solely from the auto-fluorescence of the object into video signals. For the purpose described above, the coating and the filter should preferably have total transmittance of 0.1% or lower for the excitation light.

The objective lens system may be substantially telecentric toward the image side, so that the filter and the image pickup device receive light which are substantially parallel to the optical axis of the objective lens system. The coating of the objective lens system should preferably be provided on a rearmost surface of the objective lens system. In this way, the coating and the filter receive light rays which are substantially parallel to the optical axis of the objective lens system. In other words, the incident angle of the light onto the coating and the filter can be reduced. Thus, the coating and the filter can perform as intended and intercept the excitation light.

In addition to the function of substantially shutting off the excitation light while transmitting visible light, the coating and the filter as a whole may also have a characteristic to cut off infrared light with a predetermined wavelength used for laser treatment. Thereby, even during laser treatment using an infrared light, the infrared light reflected by the object are intercepted by the coating and the filter after entering the objective lens. Consequently, no infrared light reach the image pickup device. Thus the image pickup device is free from the adverse effects caused by infrared light. Either one or both of the filter and the coating may has/have the characteristic to block infrared light.

BRIEF DESCRIPTION OF THE DRAWINGS

The invention will be described below in detail with reference to the accompanying drawings, in which.

DESCRIPTION OF THE PREFERRED EMBODIMENT

Preferred embodiments of video endoscope systems according to the present invention will be hereinafter described with reference to the accompanying drawings.

First Embodiment

Figure 1:
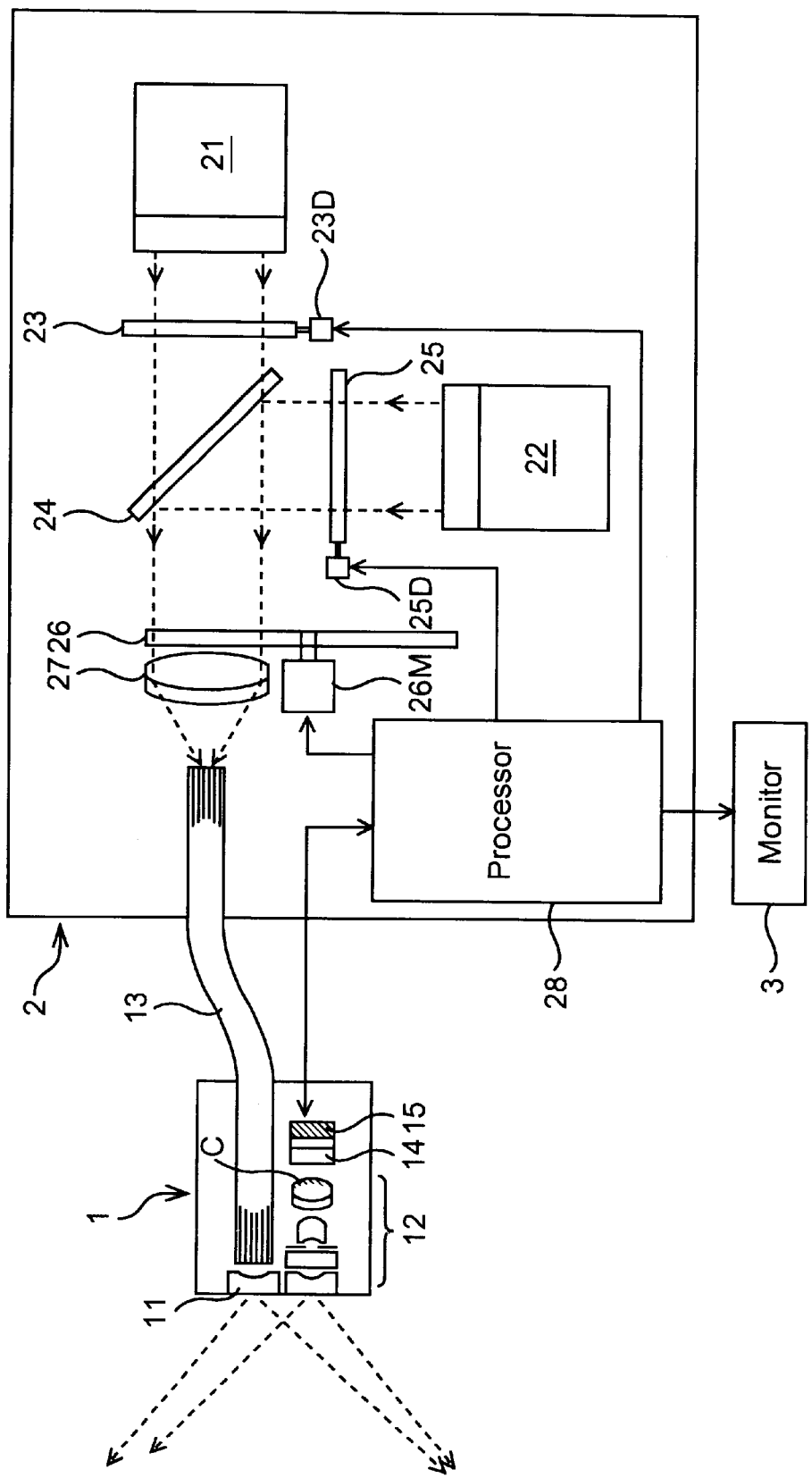
FIG. 1 is a schematic illustration showing a structure of a video endoscope system according to a first embodiment of the present invention.

FIG. 1 shows the arrangement of a video endoscope system according to a first embodiment of the present invention. The video endoscope system, as shown in FIG. 1, mainly includes a video endoscope 1, an external device 2 including a light source and a processor, and a monitor 3.

The video endoscope 1, hereinafter referred to simply as "endoscope", will be described first. Although not illustrated in FIG. 1, the endoscope 1 includes an insertion part that is formed as a flexible tube to be inserted into a body cavity, an operating part integrally connected to the proximal end of the insertion part, and a light guide flexible tube of which proximal end is integrally coupled to the operating part and of which other end is detachably connected to the external device 2. The distal end of the insertion part of the endoscope 1 is sealed with a tip member (not shown) made of a hard material. In a predetermined region near the distal end of the insertion part, a bending mechanism is incorporated (not shown). The operating part includes a dial for operating the bending mechanism to cause the distal end of the insertion part to curve, and various other operating switches. The endoscope 1 is provided with an illumination lens 11 and an objective lens system 12 in the tip member of the insertion part. The endoscope 1 also has a light guide 13 for guiding illuminating light and excitation light. The light guide 13 is a bundle of a large number of optical fibers, and led through the insertion part, operating part, and the light guide flexible tube, with its distal end opposed to the illumination lens 11. When the light guide flexible tube is connected to the external device 2, the proximal end of the light guide 13 is positioned inside the external device 2. The endoscope 1 further includes an ultraviolet and infrared cut filter 14, and a CCD (charge-coupled device) area sensor 15 serving as an image pickup device. The imaging plane of the CCD area sensor 15 (hereinafter referred to simply as CCD) is located at a position where an image of an object is formed through the objective lens system 12 when the distal end of the endoscope 1 is opposed to the object. The ultraviolet and infrared cut filter 14 is interposed between the objective lens system 12 and the CCD 15 in the optical path of the illuminating light with its one plane opposite to the imaging plane of the CCD 15.

Figure 2:
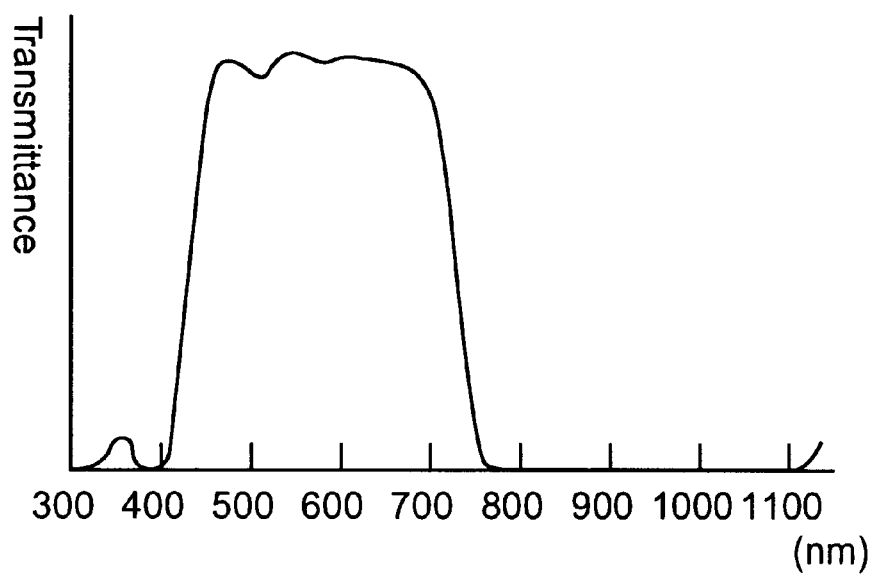
FIG. 2 is a graph showing a spectrum characteristics of an ultraviolet and infrared cut filter.

FIG. 2 is a graph showing the spectrum characteristics of the ultraviolet and infrared cut filter 14. As is evident from the graph, the ultraviolet and infrared cut filter 14 transmits the visible light rays but cuts down the ultraviolet and infrared light. Thus, the ultraviolet and infrared cut filter 14 intercepts most light rays with a wavelength within a wave range which is used for laser treatment or the like, for example a wavelength of 1064 nm by a YAG laser, or a wavelength of 810 to 890 nm by a semiconductor laser. However, while the ultraviolet and infrared cut filter 14 cuts down the ultraviolet light with a wavelength of 400 nm or lower, it still transmits some of rays of the ultraviolet light. More specifically, the transmission rate for ultraviolet light of this ultraviolet and infrared cut filter 14 exceeds 0.1%.

Figure 3:
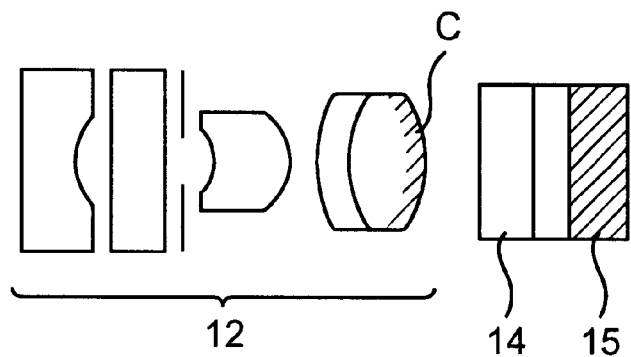
FIG. 3 is a sectional view illustrating an optical arrangement of an objective lens.
Figure 4:
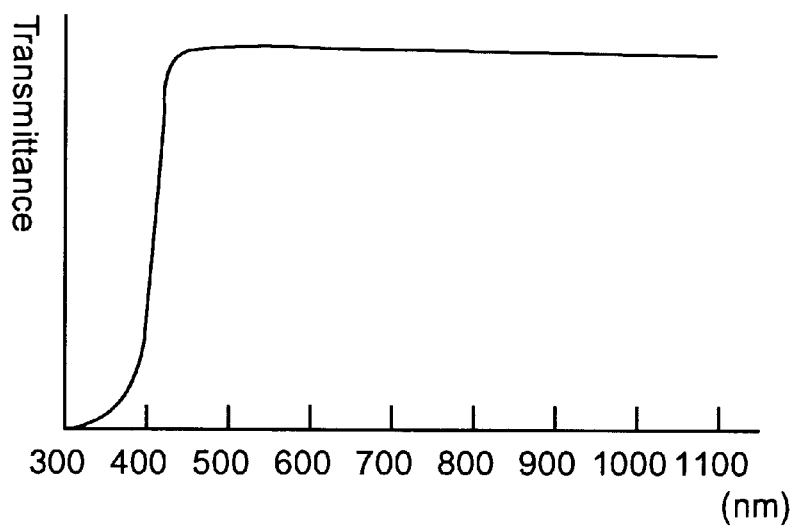
FIG. 4 is a graph showing a spectrum characteristics of an ultraviolet cut coating.

FIG. 3 is a sectional view showing an optical arrangement of the objective lens system 12. The objective lens system 12 is composed of a plurality of lenses and as a whole has a positive power. The objective lens system 12 is nearly telecentric, though not completely. Therefore, even if the principal ray of homocentric bundle of rays emitted from a point on the object and incident on the objective lens system 12 is inclined to the optical axis of the objective lens system 12, the principal ray exits from the objective lens system 12 substantially in parallel with the light axis. A rearmost lens surface of the objective lens system 12 adjacent to the image is provided with an ultraviolet cut coating C which is formed of a multilayer deposited film. FIG. 4 is a graph showing the spectrum characteristics of the ultraviolet cut coating C. As shown in FIG. 4, the coating C transmits visible light rays and infrared rays with a wavelength over 400 nm, while cutting down the ultraviolet rays with a wavelength of 400 nm or lower. Furthermore, the coating C may have a function of cutting down not only ultraviolet rays but also infrared rays, for example, when the infrared laser treatment could be performed.

Figure 5:
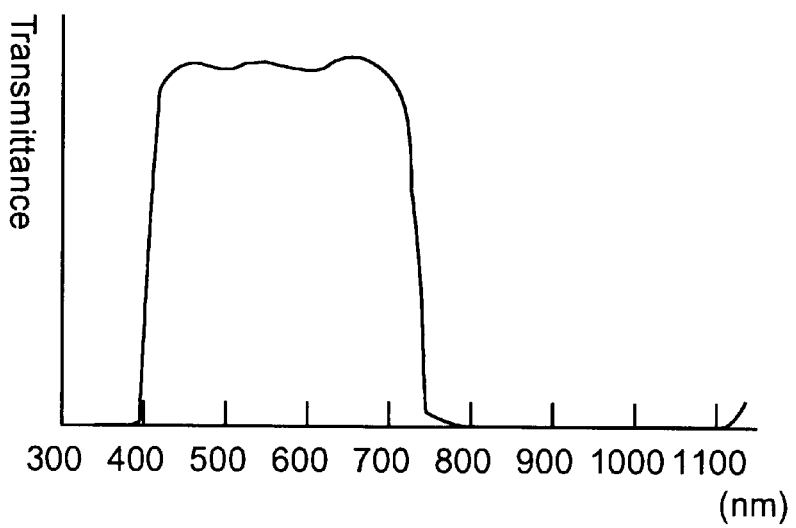
FIG. 5 is a graph showing the overall spectrum characteristics of the cut coating and the cut filter.

Thus the total transmittance for ultraviolet light becomes 0.1% or lower, in case the ultraviolet cut coating C is used in combination with the above-mentioned ultraviolet and infrared cut filter 14. FIG. 5 is a graph showing the total spectrum characteristics of the ultraviolet cut coating C and the ultraviolet and infrared cut filter 14. As is evident from the graph, by using the coating C together with the filter 14, it is possible to block the ultraviolet rays substantially completely.

The external device 2 will be described next. As shown in FIG. 1, the external device 2 includes a white light source 21 for emitting a parallel luminous flux of white light, and an excitation light source 22 for emitting a parallel luminous flux of excitation light with a wavelength within the ultraviolet wave range for exciting a living tissue to cause auto-fluorescence. A first shutter 23 and a dichroic mirror 24 are arranged sequentially in the optical path of the white light emitted from the white light source 21. A first drive mechanism 23D is joined to the first shutter 23 to move the first shutter 23 between a position where it shuts off the white light and a position out the optical path of the white light to pass. The dichroic mirror 24 reflects the light component of the ultraviolet wave range, while transmits the light component of visible wave range. The dichroic mirror 24 is inclined at 45° with respect to the optical path of the white light. The white light with a visible wave range which has passed the first shutter 23 is transmitted through the dichroic mirror 24. The excitation light source 22 is arranged so that the excitation light emitted therefrom crosses the optical path of the white light at right angles on a reflecting plane of the dichroic mirror 24. A second shutter 25 is interposed between the excitation light source 22 and the dichroic mirror 24 in the optical path of the excitation light. The second shutter 25 is moved by a second drive mechanism 25D joined thereto between a position where it shuts off the excitation light emitted from the excitation light source 22 and a position out the optical path of the excitation light to pass. The excitation light which has passed the second shutter 25 is reflected by the dichroic mirror 24. Therefore, the optical path of the excitation light reflected by the dichroic mirror 24 coincides with the optical path of the white light passing through the dichroic mirror 24.

A wheel 26 and a condenser lens 27 are arranged sequentially in the optical path in the rear of the dichroic mirror 24. The wheel 26 is a disk with four through holes (not shown) along its outer periphery. In the four holes, a blue filter transmitting light with a blue wavelength, a green filter transmitting light with green wavelength, an red filter transmitting light with red wavelength, and a transparent member transmitting the excitation light are fitted, respectively. A motor 26M is joined to the wheel 26 to rotate the same so as to cause the blue filter, green filter, red filter, and transparent member to be successively and repeatedly located in the optical path. The condenser lens 27 converges the parallel luminous flux, which has passed through the wheel 26, onto the proximal end face of the light guide 13.

The above described light sources 21, 22, shutters 23, 25, drive mechanisms 23D, 25D, dichroic mirror 24, wheel 26, condenser lens 27, light guide 13 and illumination lens 11 functions as an illumination unit.

In addition, the external device 2 includes a processor 28 which is connected to the drive mechanisms 23D, 25D, the motor 26M, and the CCD 15 of the endoscope 1. The drive mechanisms 23D, 25D and the motor 26M are thereby controlled in synchronization with each other. More specifically, during a period in which any one of the blue filter, green filter and red filter of the wheel 26 is interposed in the optical path, the processor 28 causes the drive mechanism 23D to retract the first shutter 23 so as to allow the white light to pass. At the same time, the processor 28 controls the drive mechanism 25D to move the second shutter 25 to shut off the excitation light. On the other hand, while the transparent member of the wheel 26 is interposed in the light path, the first shutter 23 is moved by the drive mechanism 23D to shut the white light. At the same time, the drive mechanism 25D moves the second shutter 25 to allow the excitation light to pass. The processor 28 controls the motor 26M to rotate the wheel 26 so that the white light, which has passed the first shutter 23 and been transmitted through the dichroic mirror 24, is converted into blue, green, and red light successively and so that the excitation light, which has passed the second shutter 25 and been reflected by the dichroic mirror 24, passes through the transparent member. Thus, blue light, green light, red light, and excitation light successively exit from the wheel 26. The light subsequently converged by the condenser lens 27 onto the proximal end face of the light guide 13 is guided through the light guide 13 and then diverged through the illumination lens 11. As a result, the surface of the object in front of the distal end face of the endoscope 1 is illuminated repeatedly with blue light, green light, red light, and excitation light in succession.

While the living tissue as the object is illuminated with the blue light, the green light, or the red light, images of the living tissue are formed from the light of each wavelength near the imaging plane of the CCD 15 by the objective lens system 12. These images are converted into video signals by the CCD 15. More specifically, images of the living tissue formed from the blue light, the green light, and the red light are respectively converted into B video signals, G video signals, and R video signals. On the other hand, while the living tissue is irradiated with the excitation light, it emits auto-fluorescence. In this case, the objective lens system 12 receives the auto-fluorescence emitted from the tissue and the excitation light reflected by the tissue surface. The component of the excitation light incident on the objective lens system 12 is substantially shut off by the ultraviolet cut coating C and the ultraviolet and infrared cut filter 14. This allows an image of the living tissue to be formed on the imaging plane of the CCD 15 solely from its generated auto-fluorescence. The CCD 15 converts this image formed from the auto-fluorescence caused by the living tissue into video signals (F video signals). The R video signal, G video signal, B video signal and F video signals output from the CCD 15 are successively and repeatedly sent to the processor 28. Thereupon, the processor 28 produces normal video data representative of color images of the living tissue based on the successively received B video signals, G video signals, and R video signals. Similarly, the processor 28 produces fluorescence video data representative of distribution of auto-fluorescence on the living tissue based on the received F video signals. The processor 28 then adjusts the levels of the R video data and fluorescence video data so that they may be almost the same and obtain a difference between the adjusted R video data and the fluorescence video data as differential video data. The differential video data contain only the video data representative of a portion of the object where the auto-fluorescence is weak. Then, the processor 28 generates video data for diagnosis by superimposing monochrome image based on the differential video data as an image of a primary color, for example blue, onto the color image based on the normal video data. Then, the video data for diagnosis is output from the processor 28. Based on this video data for diagnosis, a moving image for diagnosis is displayed on the monitor 3. The operator observes the images thus displayed to precisely determine the position and the shape of possibly malignant tissue, where the auto-fluorescence intensity is low. As an alternative, a color moving image of the tissue displayed based on the normal video data may be displayed on the monitor 3 side by side with the image provided for diagnosis.

As described above, according to the video endoscope system of this embodiment, the excitation light reflected by the surface of the object, which enters the objective lens 12, is cut down by the ultraviolet cut coating C and the ultraviolet and infrared cut filter 14. Therefore, the fluorescence video data generated by the processor 28 are regarded as being representative of an image formed solely from the auto-fluorescence caused by the object. In other words, the fluorescence video data do not contain any components caused by the excitation light. Moreover, the video endoscope system is capable of practically intercepting the excitation light without increasing the number of deposited films on the ultraviolet and infrared cut filter 14. This is because of the ultraviolet cut coating C provided on the objective lens system 12 reducing the excitation light. This eliminates the risk of cracking occurring in the ultraviolet and infrared cut filters 14 during the fabrication process of the same. This results in higher yields of the ultraviolet and infrared cut filters 14.

The ultraviolet cut coating C and the ultraviolet and infrared cut filter 14 perform as intended when a beam of light is perpendicularly incident on their surfaces. On the contrary, the coating C and the filter 14 would not perform as intended if the incident light beam were inclined at an angle which exceeds a permissible level. However, the objective lens system 12 of this embodiment is significantly telecentric toward the image side, so that, even when a beam of light enters the objective lens system 12 at a wide angle, the principal ray of each luminous flux that exits from the objective lens system 12 is substantially in parallel with its optical axis. This restricts the incident angle of the light onto the ultraviolet cut coating C and the ultraviolet and infrared cut filter 14 to within a permissible range. Thus, it is ensured that the ultraviolet cut coating C and the ultraviolet and infrared cut filter 14 can cut off the incident excitation light as intended.

The operator can treat a diseased portion of the object of examination while observing the images displayed on the monitor 3. For example, infrared laser treatment could be performed on the diseased portion with a laser probe irradiating an infrared laser beam. The infrared rays emitted from the laser probe may be reflected by the surface of the diseased portion and enter the objective lens system 12 of the endoscope 1. Even is the case, the reflected infrared rays are intercepted by the ultraviolet and infrared cut filter 14 and cannot reach the CCD 15. Thus the images displayed on the monitor 3 will not be disturbed even during the laser treatment operation.

Second Embodiment

Figure 6:
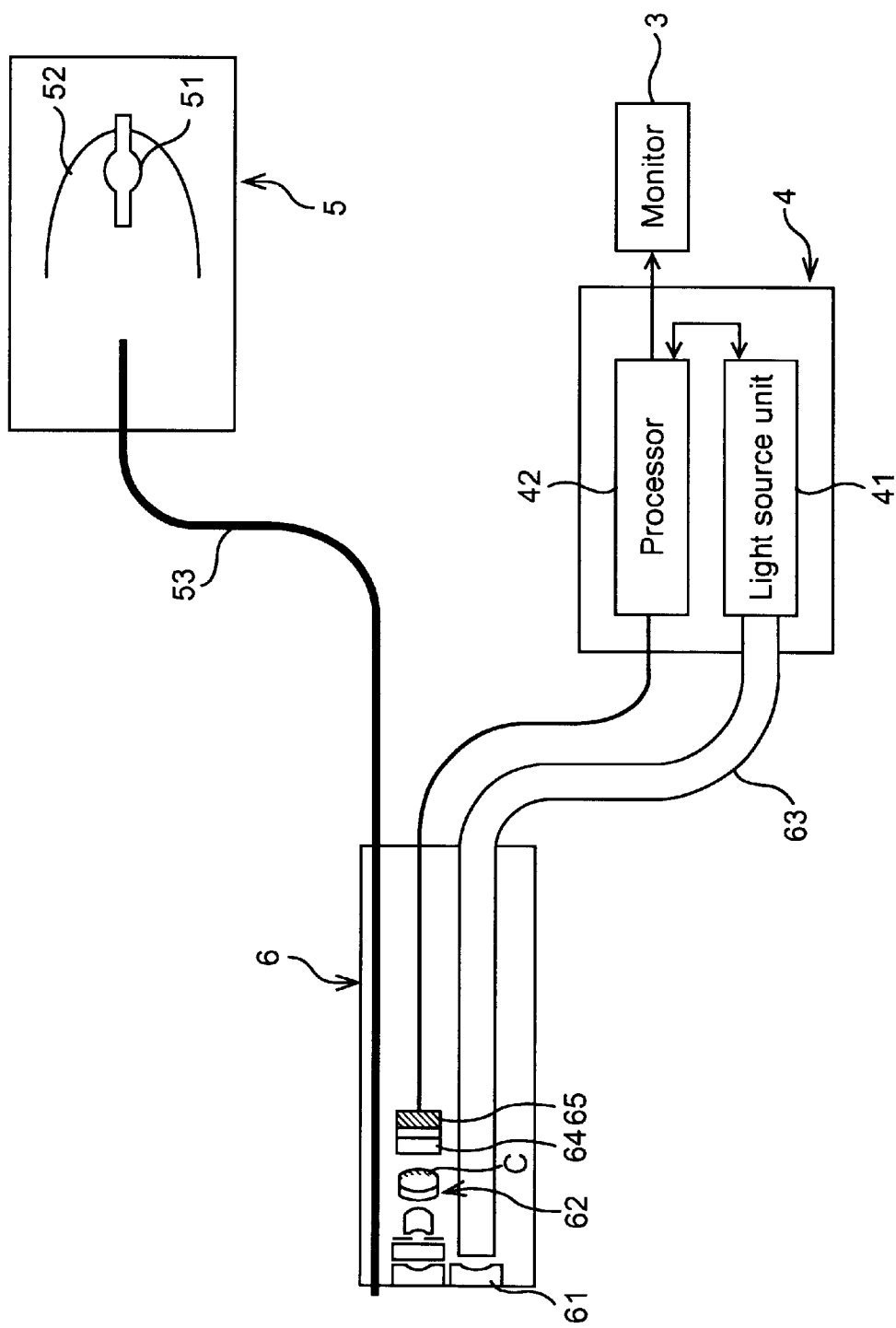
FIG. 6 is a schematic illustration the arrangement of a video endoscope system according to a second embodiment of the present invention.

FIG. 6 is a diagram illustrating the arrangement of a video endoscope system according to a second embodiment of the present invention. The system includes, as shown in FIG. 6, a video endoscope 6, an external device 4 including a light source and a processor, an excitation light source device 5, and a monitor 3.

The video endoscope 6, hereinafter referred to simply as "endoscope", includes a an insertion portion of which concrete shape is not illustrated in FIG. 6 and which is formed as a flexible tube to be inserted into a body cavity, and an operating part integrally connected to the proximal end of the insertion part. The video endoscope 6 also includes a light guide flexible tube of which proximal end is integrally coupled to the operating part, and of which other end is detachably connected to the external device 4. Similar to the first embodiment described above, the endoscope 6 is provided with an illumination lens 61 and an objective lens system 62 in the tip member of the insertion part. The objective lens system 62 is provided with an ultraviolet cut coating C of which spectrum characteristics are as shown in the graph of FIG. 4. The endoscope 6 also has a light guide 63, which is a bundle of a large number of optical fibers. The light guide 63 is led through the insertion part, operating part, and the light guide flexible tube, with its distal end opposed to the illumination lens 61. When the light guide flexible tube is connected to the external device 4, the proximal end of the light guide 63 is positioned inside the external device 4. In the insertion part of the endoscope 6, an ultraviolet and infrared cut filter 64 and a CCD 65 are arranged, in order in the rear of the objective lens system 62, similar to the first embodiment. The ultraviolet and infrared cut filter 64 has spectrum characteristics shown in the graph of FIG. 2. The total spectrum characteristics of the ultraviolet cut coating C and the ultraviolet and infrared cut filter 64 are as shown in the graph of FIG. 5.

To the CCD 65 is connected a signal cable through which video image signals obtained by the CCD 65 are transmitted. The signal cable is led through the insertion part, operating part, and light guide flexible tube together with the light guide 63. With the light guide flexible tube connected to the external device 4, the terminal end of the signal cable is electrically connected to a signal terminal inside the external device 4.

The external device 4 includes a light source unit 41 and a processor 42. The light source unit 41 includes a white light source, and a wheel for converting the white light emitted from the light source successively into blue, green and red light, although not shown in the drawing. The processor 42 is connected to both of the light source unit 41 and the monitor 3.

With the light guide flexible tube of the endoscope 6 connected to the external device 4, the proximal end of the light guide 63 faces the light source unit 41, while the CCD 65 is connected to the processor 42. In this state, the light source unit 41 successively and repeatedly projects blue, green and red light to be entered into the proximal end of the light guide 63 which faces the light source unit 41. The incident light rays are transmitted through the light guide 63 and then diverged through the illumination lens 61. Thus, the living tissue as the object facing the distal end of the insertion part of the endoscope 6 is illuminated successively and repeatedly with blue, green, and red light. As a result, the light of each wavelength reflected by the surface of the living tissue forms images of the living tissue near the imaging plane of the CCD 65 through the objective lens system 62. These images are converted into video signals by the CCD 65. More specifically, images of the living tissue formed from the blue light, the green light and the red light are converted into B video signals, G video signals, and R video signals. The processor 42 produces normal video data representative of color images of the living tissue based on the successively received B video signals, G video signals, and R video signals. Thereupon, a color moving image of the living tissue is displayed on the monitor 3 based on the normal video data.

The endoscope 6 further includes a forceps channel composed of a pair of apertures one of which opens at the tip member and the other at the operating part of the endoscope 6, and a tube connecting these apertures. The operator can lead an excitation light guide, to be described below, forceps, instruments, or various other probes through the forceps channel to make tip end of them project from the distal end face of the insertion part of the endoscope 6.

The excitation light source unit 5 corresponds to the illumination unit and includes an ultraviolet lamp 51, a reflector 52, and the excitation light guide 53 mentioned above. The ultraviolet lamp 51 is a light source for emitting light with a wavelength within an ultraviolet wave range for exciting a living tissue to cause auto-fluorescence. The reflector 52 is a reflection mirror which is symmetrical with respect to its rotational axis, and which has a reflecting plane on its inner surface. The excitation light guide 53 is a bundle of a large number of optical fibers. The excitation light guide 53 is led through the forceps channel of the endoscope 6 with its proximal end facing the reflector 52 so that its distal end may be projected from the distal end face of the insertion part of the endoscope 6.

When the operator turns on the ultraviolet lamp 51 while turning off the light source unit 41, the excitation light emitted from the ultraviolet lamp 51 is reflected by the reflector 52 and converged on the proximal end face of the excitation light guide 53 which faces the reflector 52. The converged excitation light is transmitted through the excitation light guide 53 and projected from its distal end face, toward a living tissue as an object of examination. Irradiated with the excitation light, the living tissue causes auto-fluorescence. The objective lens system 62 receives both the auto-fluorescence caused by the living tissue and the excitation light reflected by the surface of the living tissue. The component of the excitation light incident on the objective lens system 62 is substantially shut off by the ultraviolet cut coating C on the objective lens system 62 and the ultraviolet cut coating filter 64. Therefore, an image of the living tissue is formed solely from the auto-fluorescence on the imaging plane of the CCD 65. The CCD 65 converts this image into video signals (F video signals).

Thereupon, the processor 42 generates fluorescence video data representative of distribution of auto-fluorescence on the living tissue based on the F video signals output from the CCD 65. Thus, a moving image of the living tissue formed from the auto-fluorescence is displayed on the monitor 3 based on the fluorescence video data.

In the video endoscope system of the above-described embodiments, a so-called RGB frame sequential system is adopted, in which an object of examination is illuminated successively with the blue light, the green light and the red light so as to generate normal color images of the object based on the RGB video signals obtained by the CCD 15.

As another method for obtaining color images of an object, that using a color CCD which is a CCD area sensor equipped with a color mosaic filter is practiced. The color CCD converts an image of an object illuminated with white light into color video signals. It is known that the color CCD outputs favorable video signals when the incident light rays are perpendicular to its imaging plane. Therefore, it should preferably be used with an objective lens, which is completely telecentric. Accordingly, if the video endoscope system uses such color CCD, its objective optical system should preferably have an objective lens which is telecentric toward the image side, and an ultraviolet and infrared cut filter 14 interposed between the objective lens and the color CCD in the optical path. Also in this case, the rearmost lens surface of the objective lens system should be provided with an ultraviolet cut coating C similarly to the objective lens system 12 of the above-described embodiments. Thereby, when the auto-fluorescence is caused by the living tissue illuminated with the excitation light, the excitation light reflected by the surface of the living tissue is cut off by the ultraviolet cut coating C and the ultraviolet and infrared cut filter 14. As a result, the excitation light is reduced to 0.1% or lower.

As evident from above, the video endoscope according to the present invention can reduce the excitation light to 0.1% or lower not only with an ultraviolet and infrared cut filter inserted in the optical path between the objective lens and the image pickup device, but also with an ultraviolet cut coating provided on a lens surface of the objective lens system. Accordingly, the video endoscope system according to present the invention is capable of outputting fluorescence video data free from the influence of the excitation light.

We claim:

1. A video endoscope, comprising:
   an objective lens system having a lens surface provided with a coating that transmits a visible light while reducing an excitation light that excites a living tissue to cause auto-fluorescence, said coating being provided on a rearmost surface of said objective lens system, said objective lens system being telecentric toward an image side;
   an image pickup that concerts an image of an object formed through said objective lens system into video signals; and
   a filter interposed between said objective lens system and said image pickup to transmit the visible light while reducing the excitation light.

2. The video endoscope of claim 1, wherein a total transmittance of said coating and said filter for excitation light does not exceed approximately 0.1%.

3. The video endoscope of claim 1, wherein said filter reduces an infrared light with a predetermined way length used for laser treatment.

4. The video endoscope of claim 1, wherein said coating reduces an infrared light with a predetermined wavelength used for laser treatment.

5. A video endoscope system, comprising:
   a video endoscope which includes an objective lens system having a lens surface provided with a coating that transmits a visible light while reducing an excitation light that excites a living tissue to cause auto-fluorescence, an image pickup that converts an image of an object formed through said objective lens system into a video signal, and a filter interposed between said objective lens system and said image pickup to transmit the visible light while reducing the excitation light;
   an illuminating unit which irradiates excitation light to the object; and
   a processor which generates and outputs fluorescence video data corresponding to an image of the object formed from the auto-fluorescence caused by the object, based on the video signal obtained by said image pickup, wherein said coating is provided on a rearmost surface of said objective lens system, and said objective lens system is telecentric toward an image side.

6. A video endoscope system, comprising:
   a video endoscope which includes an objective lens system having a lens surface provided with a coating that transmits a visible light while reducing an excitation light that excites a living tissue to cause auto-fluorescence, an image pickup that converts an image of an object formed through said objective lens system into a video signal, and a filter interposed between said objective lens system and said image pickup to transmit the visible light while reducing the excitation light;
   an illuminating unit which irradiates the visible light and the excitation light alternately and repeatedly toward the object; and
   a processor which generates and outputs normal video data based on part of the video signal obtained by the image pickup during a period in which the visible light is irradiated from said illuminating unit, and fluorescence video data based on part of the video signal obtained by the image pickup during a period in which the excitation light is irradiated from said illumination unit, wherein said coating is provided on a rearmost surface of said objective lens system, and said objective lens system is telecentric toward an image side.

7. The video endoscope system of claim 5, further comprising a monitor that displays the image based on the fluorescence video data output from said processor.

8. A video endoscope, comprising:
   an objective lens system including a coating provided at a position where a principal ray of a luminous flux exiting from the objective lens system is substantially parallel with its optical axis, said at least one of said optical filter and said coating transmitting a visible light while reducing an excitation light; and
   an image pickup that con an image of an object formed through said objective lens system into a video signal wherein the position of said coating comprises a rearmost surface of said objective lens system.

9. The video endoscope of claim 8, wherein said optical filter reduces an infrared light with a predetermined wavelength.

* * * * *